United States Patent [19]

Quaas

[11] 4,295,476
[45] Oct. 20, 1981

[54] BLOOD COLLECTION ASSEMBLY FOR PREVENTING OUTWARD MOVEMENT OF THE BLOOD CONTAINER

[75] Inventor: Gary F. Quaas, Rutherford, N.J.

[73] Assignee: Becton, Dickinson and Company, Paramus, N.J.

[21] Appl. No.: 105,346

[22] Filed: Dec. 19, 1979

[51] Int. Cl.³ .............................................. A61B 5/14
[52] U.S. Cl. .................................. 128/764; 128/766; 128/218 D
[58] Field of Search ............................... 128/760–767, 128/218 D

[56] References Cited

U.S. PATENT DOCUMENTS

| 2,437,408 | 3/1948 | Soet | 128/764 |
| 2,484,657 | 10/1949 | Son | 128/218 D |
| 3,366,103 | 1/1968 | Keller | 128/764 |
| 3,469,572 | 9/1969 | Nehring | 128/764 |
| 3,503,386 | 3/1970 | Pieratt | 128/764 |
| 3,604,410 | 9/1971 | Whitacre | 128/762 |
| 4,140,108 | 2/1979 | Nugent | 128/760 |
| 4,150,666 | 4/1979 | Brush | 128/763 |
| 4,227,528 | 10/1980 | Wardlaw | 128/218 D |

*Primary Examiner*—Kyle L. Howell
*Attorney, Agent, or Firm*—Richard J. Rodrick

[57] ABSTRACT

A blood collection assembly for use with a blood collection container which includes a cannula-penetrable closure with a lip element associated therewith. Included in this assembly is a receptacle having a closed end and an open end for the receipt of the blood collection container, and a peripheral surface between the ends. A cannula extends from the closed end into the receptacle and also extends outwardly from the closed end of the receptacle. A spring-resilient valve sheath may cover the inwardly extending cannula for control of fluid through the cannula. A spring-depressible tongue is connected to the peripheral surface of the receptacle and is inwardly depressible for engaging the lip element on the blood collection container to prevent outward movement of the container during the blood collecting procedure.

7 Claims, 4 Drawing Figures

BLOOD COLLECTION ASSEMBLY FOR PREVENTING OUTWARD MOVEMENT OF THE BLOOD CONTAINER

BACKGROUND OF THE INVENTION

The present invention relates to a blood collection assembly for use with a blood collection container, and more particularly, concerns a blood collection assembly which maintains the blood collection container in fixed position during the blood collecting procedure thereby preventing the container from being pushed outwardly during such procedure.

Many blood collection assemblies are used nowadays for taking multiple blood samples from a patient. Various types of these blood collection assemblies or blood sampling devices are very well known in the art. Generally speaking, these blood collection assemblies include a receptacle or tubular holder into which a blood collection container or tube is received. A needle cannula extends through the receptacle's closed end, the cannula having an external point and an internal point. The external point is for insertion of the cannula into the vein of the patient, whereas the interior point is meant to puncture the penetrable closure which generally stoppers the open end of the blood collection container. Thus, by sliding the collection container into the open end of the collection receptacle, the interior point of the cannula pierces the closure of the container and can thereby deliver blood into the container.

One particular problem which arises in this general type of blood collection assembly concerns the maintenance of the container in a substantially fixed position while inserted in the receptacle. There is a tendency for the container to back off or push out of the receptacle, perhaps due to the penetration forces of the cannula through the penetrable closure of the blood container. With this occurrence, it becomes necessary for the operator of the blood collection assembly to maintain both hands on the entire assembly, one hand holding the receptacle in place in the patient, the other hand holding the blood collection container in position within the receptacle of the collection assembly.

This occurrence of blood collection container push out has become greatly magnified in those instances where the collection assembly includes a spring-resilient valve sheath covering the interior cannula inside the receptacle. This type of valve sheath has become more prevalent especially in the collection assemblies for taking multiple blood samples. The sheath is generally a thin, flexible elastomeric material with self-sealing properties; it covers the interior cannula and thereby prevents blood or other fluids from flowing through the cannula. When the blood collection container is inserted into the receptacle, the leading edge of the closure pushes against the sheath so that the point of the interior cannula pierces the sheath and also penetrates the closure itself. Further inward movement of the blood container then effectively squeezes the sheath, in accordion-like fashion, against the closed end of the receptacle. When the blood collection container is withdrawn, the resiliency of the sheath forces the same to return to its normal relaxed condition, covering the interior cannula and effectively serving as a valve to prevent blood from flowing therethrough. This is most effective for allowing multiple blood sampling, wherein the first blood collection container has to be withdrawn and then another collection container re-inserted into the receptacle. This type of valve sheath is disclosed, for instance, in U.S. Pat. Nos. 3,469,572; 4,136,794; and 4,140,108.

It can be appreciated that every time the blood collection container forces the spring-resilient sheath into its compressed, accordion-like fashion, the sheath serves as a loaded spring. If the operator of the blood collection assembly fails to hold the collection container in a properly seated condition, the compressed sheath has a tendency to urge the collection container outwardly to push the same, perhaps off and away from the interior cannula. This would thereby result in no blood being collected inside the container. Accordingly, this type of blood collection assembly with such a spring-resilient valve sheath, has heretofore demanded that the operator keep both hands on the assembly in order to keep it functioning properly. It can also be appreciated, that when the operator has to push inwardly against the collection container for proper usage, this could cause accidental, deeper penetration of the exterior cannula into the vein of the patient. Thus, this inward pushing against the collection container may give rise to more instances of potential injury to the patient, or else cause traumatic effects to the vein being tapped. With the foregoing in mind, there is a demand for effectively maintaining the blood collection container in proper position in the collection assembly while, at the same time, eliminating the need to constantly exert an inward force against the container. It is to the solution of this problem, which heretofore has been basically unsolved, that the present invention is directed.

SUMMARY OF THE INVENTION

A blood collection assembly for using with a closed blood collection container one end of which includes a cannula-penetrable closure with a lip element associated therewith. This assembly comprises receptacle means having a closed end and an open end for the receipt of the blood collection container, and a peripheral surface between the ends. Cannula means extends from the closed end into the receptacle and extends outwardly from the closed end with a needle point on each respective end of the cannula means. Spring-depressible means is connected to the peripheral surface of the receptacle means being inwardly depressible for engaging the lip element on the blood collection container to thereby prevent outward movement of the container during the blood collecting procedure.

The spring-depressible means for preventing blood container movement is most advantageous when used in a blood collection assembly embodiment which includes spring-resilient valve means externally associated with the inwardly extending cannula means. This valve means is adapted to prevent fluid flow through the cannula when it is in the relaxed condition and is activatable to expose the needle point of the inwardly extending cannula means to permit fluid flow therethrough.

In the preferred embodiment of the present invention, the receptacle means is a plastic, cylindrically shaped receptacle including at least one spring-depressible, substantially rectangularly shaped tongue integrally hinged to a side wall of the receptacle. This tongue has a distal end depressible inwardly into the interior of the receptacle and is adapted to spring back to be substantially flush with the side wall when a depression force is removed from the tongue. The distal end of the tongue is adapted to engage the lip element on the blood collection chamber. This thereby prevents the container from being pushed out of the receptacle under the influence of the spring force of the resilient valve surrounding the interior cannula during the blood collecting procedure. There may, of course, be more than one spring-depressible tongue in the receptacle of this assembly.

From the structural standpoint, the blood collection assembly of the present invention is notably different from prior art blood collection assemblies, particularly those useful for multiple blood sampling techniques. In particular, the spring-depressible tongue is provided to particularly oppose any forces against the blood collection container which tend to urge the container outwardly from the blood collection receptacle. These outwardly directed forces are quite significant in those instances when a spring-resilient valve sheath is included in the collection assembly surrounding the interior cannula. Accordingly, the depressible tongue serves to lock the blood collection container into proper position to ensure that there is an uninterrupted blood draw. In addition, once the blood collection container is maintained in a fixed position so that there is no outward movement thereof, the operator need not keep both hands on the blood collection assembly when drawing blood. As pointed out above, prior blood collection assemblies, especially those with a valve sheath around the interior cannula, virtually required the use of both hands of the operator. Furthermore, the depressible tongue feature of the present invention provides engagement/disengagement of a locking system which requires no additional hand repositioning than that used on presently existing blood collection assemblies. Also, by locking the blood collection container into position, the potential for injury to the patient by constant inward pushing of the container has been eliminated by the features of the present invention. As a further advantage, the present invention is convenient to use due, in particular, to its straightforward construction.

DETAILED DESCRIPTION

Figure 1:
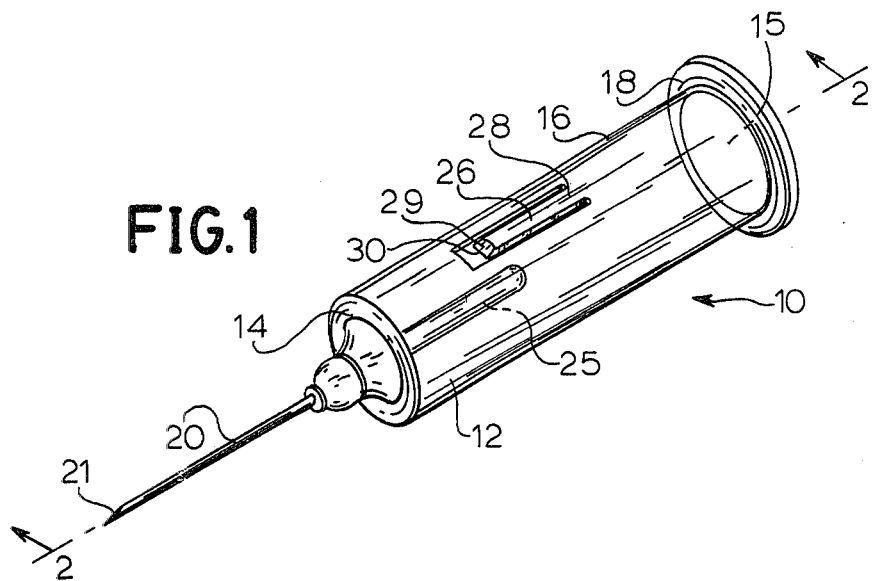
FIG. 1 is a perspective view of the preferred blood collection assembly of the present invention.

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Figure 2:
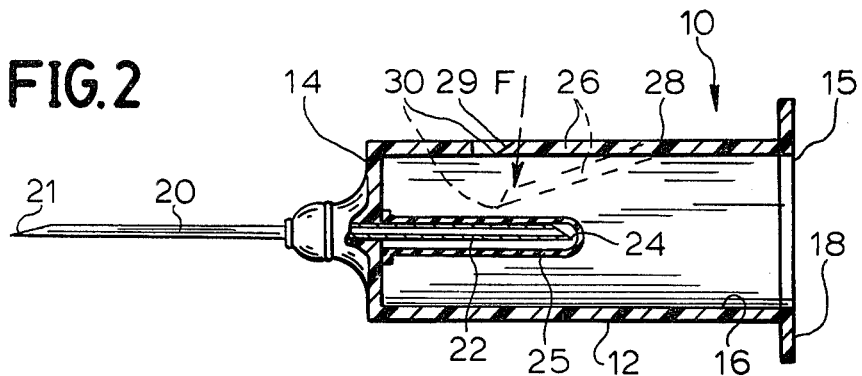
FIG. 2 is a cross-sectional view taken along line 2—2 of FIG. 1.

Referring to the drawings, particularly FIGS. 1 and 2, there is illustrated the preferred embodiment of a blood collection assembly 10. Collection assembly 10 is comprised of a substantially cylindrical, preferably plastic, receptacle 12, generally somewhat elongate in nature so as to properly receive a blood collection container therein. One end of receptacle 12 is a closed end 14 with the opposite end being an open end 15 for the receipt of the blood collection container. Between the ends of the receptacle is a peripheral side wall 16, preferably cylindrically configured. An annular rim 18 surrounds open end 15 and is provided to facilitate gripping of the collection assembly by the operator during the blood collection procedure. The interior surfaces of receptacle 12 are usually smoothly finished so that the blood collection containers can be easily slid in and out of the receptacle.

Extending outwardly from closed end 14 is an exterior cannula 20 with a sharp needle point 21 at its end. Extending inwardly from closed end 14 into receptacle 12 is an interior cannula 22 having a sharp needle point 24 at its end. Cannulae 20 and 22 may be two separate cannulae mounted in the closed end so that their respective lumens are in fluid communication with each other. Or, on the other hand, cannulae 20 and 22 may be portions of a single double ended needle cannula mounted in closed end 14 so that a portion 20 extends outwardly and a portion 22 extends inwardly. Those skilled in the art will recognize that exterior cannula 20 is intended for insertion into the patient in order to collect blood, whereas interior cannula 22 is intended to pierce a closure of the blood collection container for delivering blood from the patient into the container.

Surrounding interior cannula 22 is a valve sheath 25 which normally covers the entire interior cannula when in its relaxed condition, thereby serving as a closed valve to prevent fluid flow through the cannula. The preferred valve sheath is a spring-resilient, cannula-penetrable, self-sealing elastomeric material. This type of sheath is most effective in permitting the blood collection assembly to be used for multiple blood sampling, inasmuch as each time a blood collection container is removed from the receptacle the sheath springs back over the interior cannula to effectively close off blood flow. Sheaths of this nature, their functions and properties are described in the aforementioned patents.

Included in peripheral side wall 16 of the receptacle is a spring-depressible tongue 26. In the embodiment being described, tongue 26 is substantially rectangularly shaped element which is preferably integrally molded into the side wall of the receptacle during the fabrication process. Tongue 26 is thereby formed by having three sides of the rectangular section separated from side wall 16 with the fourth side 28 remaining connected to side wall 16. Connected side 28 of the tongue thus serves as an integral hinge for depression of the tongue. It is appreciated that the tongue of substantially rectangular shape is merely a preferred embodiment, and that other shapes, such as triangular, oval, circular, square and even irregular, may be utilized. It can be seen, then, with connected side 28 serving as a hinge the distal end 29 of the tongue is depressible inwardly into the interior of receptacle 12 upon the application of a depression force as designated by letter F in FIG. 2. The inwardly depressed condition of tongue 26 is shown by the phantom lines in FIG. 2. It is preferred that tongue 26 be spring-depressible so that it is adapted to spring back to be substantially flush with side wall 16 of the receptacle when the depression force is removed from the tongue. This flush condition is the normal condition of the tongue when no depression force is being applied. In order to facilitate the engagement of the depressed tongue to the blood collection container when inserted in the receptacle, distal end 29 of the tongue (facing toward closed end 14) is preferably beveled to form a point 30. As an alternative, or in addition to such a point, distal end 29 may be serrated to provide proper engagement of the tongue to the blood collection container. While only one depressible tongue is illustrated in the side wall of the receptacle in this embodiment being described, it is appreciated that there may be a plurality of spring-depressible tongues around the periphery of the receptacle. In such case, the operator of the blood collection assembly may choose to use one or more of the depressible tongues for locking purposes, but not necessarily all, thereby providing more flexibility and convenience to the user.

Figure 3:
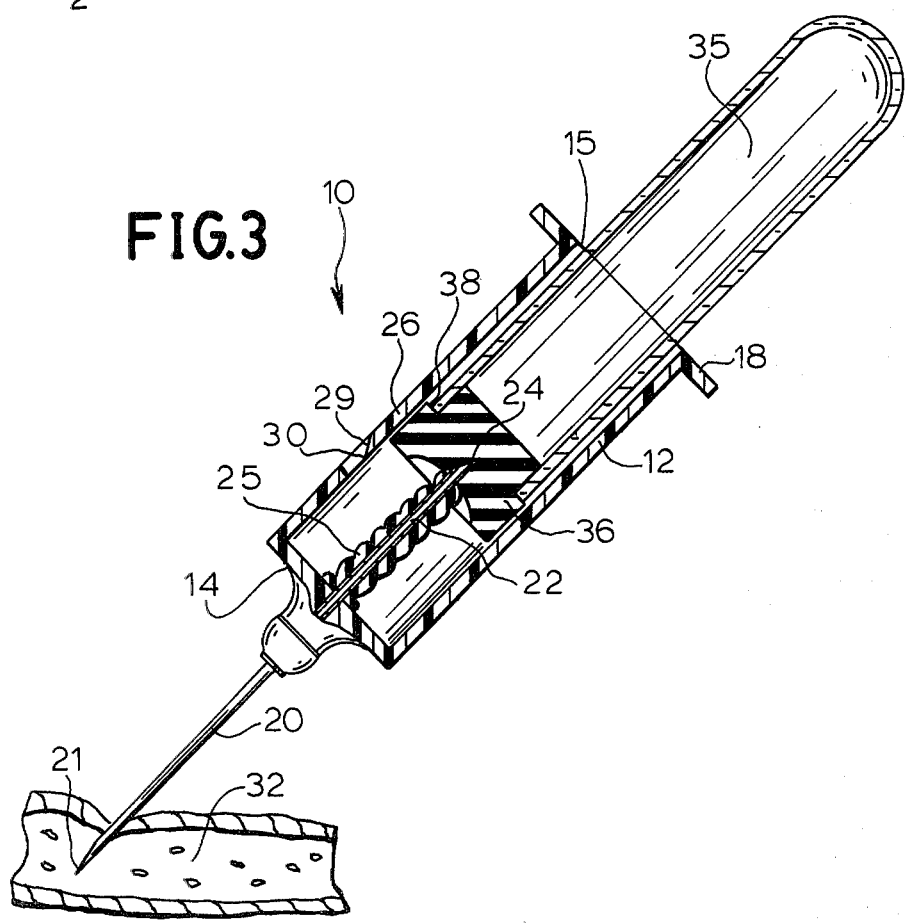
FIG. 3 is a cross-sectional view of the blood collection assembly of FIG. 1 with a blood collection container being inserted into the collection assembly during the blood collection procedure.
Figure 4:
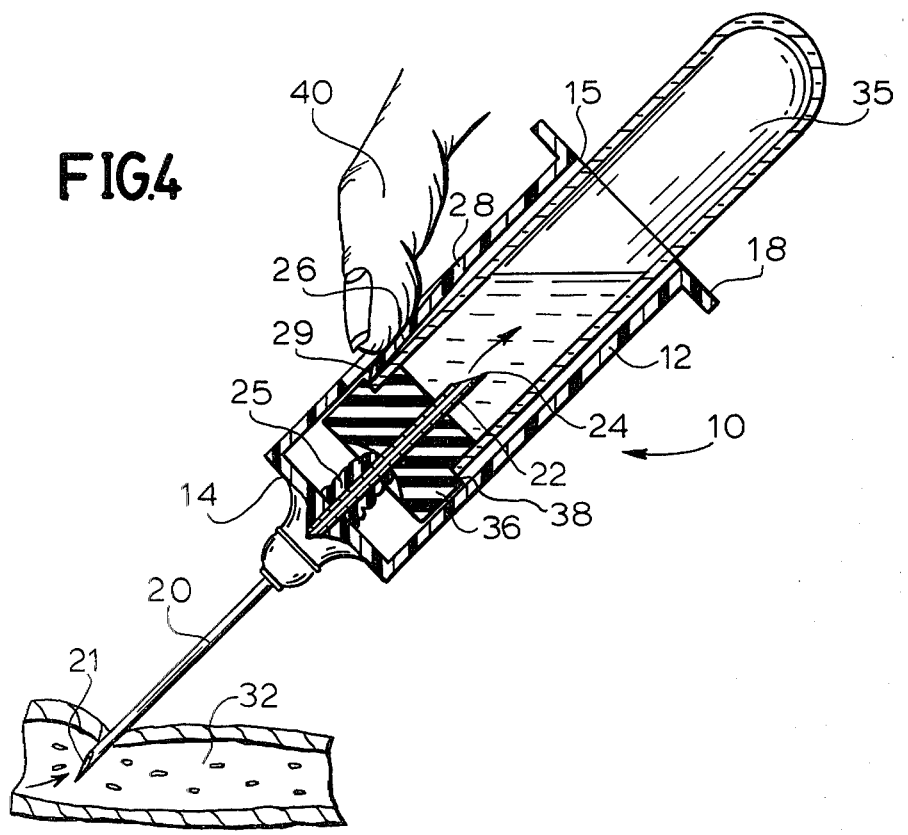
FIG. 4 is a cross-sectional view in sequence to FIG. 3 illustrating the blood collection container being fixed into position by the operator during the blood collecting procedure.

Turning now to FIGS. 3 and 4, blood collection assembly 10 of the present invention is illustrated in use during the blood collecting procedure. Referring specifically to FIG. 3, needle point 21 of exterior cannula 20 has penetrated blood vessel 32 and is in position to draw blood therefrom. Before blood collection container 35 is inserted into receptacle 12 valve sheath 25 covers interior cannula 22 and prevents blood from flowing out of the interior cannula into the empty receptacle. It can be seen in FIG. 3 that blood collection container 35 is being slid through open end 15 of the receptacle 12 toward closed end 14. The collection container is generally an air evacuated blood collection tube one end of which includes a cannula-penetrable closure 36. A flange is usually provided at or near the top surface of closure 36 to assist in providing an effective seal by providing an abutment against the top end of the blood collection tube. This flange thereby serves as an annular lip 38 around the end of the blood collection container, and is usually found in most blood collection containers which are used for the purposes being described herein. In most instances, the fit between the peripheral surface of closure 36 and the inside surface of receptacle 12 is fairly close so as to eliminate excessive free play therebetween.

It can also be seen in FIG. 3 that the leading edge of closure 36 has been forced against interior cannula 22 so that its point 24 penetrates through valve sheath 25 and starts to penetrate closure 36 of the blood collection container. Valve sheath 25 then becomes compressed in the space between closed end 14 of the receptacle and the leading face of closure 36. At this time, depressible tongue 26 merely remains in its normally flush condition in the peripheral surface of the receptacle.

With reference to FIG. 4, blood collection container 35 has been inserted to its proper position within receptacle 12 so that needle point 24 of interior cannula 22 is completely through closure 36. Blood from vessel 32 is communicated through exterior cannula 20 and interior cannula 22 for delivery to the collection container. Valve sheath 25 is compressed against closed end 14 of the receptacle by the leading edge of closure 36. It can be appreciated that the compressed nature of this resilient valve sheath serves as a loaded spring exerting an outward influence or force against the blood collection container. To oppose and effectively overcome this spring force, the operator of the collection assembly, by using pressure with his thumb 40, inwardly depresses tongue 26 so that its distal end 29 engages lip element 38 around the blood collection container. The force exerted by spring-loaded valve sheath 25, particularly in conjunction with a pointed or serrated distal end of the tongue, maintains the tongue depressibly engaged against the lip element of the collection container during the blood collecting procedure. When the blood sample has been collected, the operator need only impart a slight axially inward movement to the collection container which will serve to separate the distal end of the tongue from the lip. Inasmuch as tongue 26 is spring-resilient, it will then spring back to its normal position substantially flush with the peripheral surface of the receptacle. This then allows the operator to withdraw the blood collection container from the receptacle.

While use of the depressible tongue feature of the present invention is most advantageous when a spring-resilient valve sheath is utilized in conjunction with the interior cannula, it also finds utility in those blood collection assemblies without such a valve sheath. For instance, effective contact between the distal end of the tongue and the lip element of the collection container can still serve to prevent premature pull out of the container during the blood collecting procedure.

Thus, the blood collection assembly of the present invention provides a convenient means for preventing undesirable outward movement of the blood collection container from the receptacle during the blood collecting procedure which thereby significantly contributes to an uninterrupted blood draw.

What is claimed is:

1. A holder assembly for use with a closed blood collection container one end of which includes a cannula-penetrable closure with a lip element associated therewith, said assembly comprising:

a receptacle having a closed end, side walls and an open end for the receipt of said blood collection container;

an interior cannula extending from said closed end into said receptacle;

an exterior cannula extending outwardly from said closed end, said interior and said exterior cannulae being in fluid communication with each other;

a spring-resilient, cannula-penetrable valve sheath covering said interior cannula adapted to expose said interior cannula to fluid flow therethrough when said blood collection container is inserted into said receptacle thereby causing said interior cannula to penetrate said closure and said sheath to become compressed against said closed end, said sheath serving as a loaded spring when compressed; and said receptacle including a spring-depressible tongue located in a side wall thereof and being normally flush with the side wall and having a distal end depressible downwardly into the interior of said receptacle and a proximal end hingedly connected to said side wall, said distal end of said tongue being spaced a pre-determined distance from the closed end of said receptacle so that it, upon being downwardly depressed, is adapted to engage said lip element on said blood collection container after being inserted into said receptacle to thereby prevent said container from being pushed out of said receptacle under the influence of the spring force of said compressed valve sheath.

2. The assembly of claim 1 wherein said sheath is a self-sealing elastomeric material normally covering the entire interior cannula when in its relaxed condition to prevent fluid flow through said interior cannula.

3. The assembly of claim 1 wherein said receptacle is made of plastic material.

4. The assembly of claim 1 wherein said tongue is a substantially rectangular section of said side wall formed by having three sides of said rectangular section separated from said side wall with the fourth side thereof remaining connected to said side wall to serve as an integral hinge for depression of said tongue.

5. The assembly of claim 1 wherein said receptacle is cylindrically shaped.

6. A holder assembly for use with a closed blood collection container one end of which includes a cannula-penetrable closure with a lip element associated therewith, said assembly comprising:

a substantially cylindrical, plastic receptacle having a closed end, side walls and an open end for the receipt of said blood collection container;

an interior cannula extending from said closed end into said receptacle;

an exterior cannula extending outwardly from said closed end, said interior and said exterior cannulae being in fluid communication with each other;

a spring-resilient, cannula-penetrable, self-sealing, elastomeric valve sheath normally covering said interior cannula in its relaxed condition adapted to expose said interior cannula to fluid flow therethrough when said blood collection container is inserted into said receptacle thereby causing said interior cannula to penetrate said closure and said sheath to become compressed against said closed end, said sheath serving as a loaded spring when compressed; and said receptacle including at least one spring-depressible, substantially rectangularly shaped tongue integrally hinged at its proximal end to a side wall thereof and having a distal end depressible downwardly into the interior of said receptacle and adapted to automatically return to its normally flush condition with said side wall when a depression force is removed from said tongue, said distal end of said tongue being spaced a predetermined distance from the closed end of said receptacle so that it, upon being downwardly depressed, is adapted to engage said lip element on said blood collection container after being inserted into said receptacle to thereby prevent said container from being pushed out of said receptacle under the influence of the spring force of said compressed valve sheath during the blood collection procedure.

7. The assembly of claim 1 or 6 wherein the distal end of said tongue is beveled to form a point to facilitate its engagement to the lip element on said blood container.

* * * * *